US011185312B2

(12) United States Patent
Nakamura (10) Patent No.: US 11,185,312 B2
(45) Date of Patent: Nov. 30, 2021

(54) MEDICAL IMAGE CAPTURING CONTROL DEVICE, METHOD, AND PROGRAM

(71) Applicant: FUJIFILM Corporation, Tokyo (JP)

(72) Inventor: Keigo Nakamura, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 468 days.

(21) Appl. No.: 15/868,610

(22) Filed: Jan. 11, 2018

(65) Prior Publication Data

US 2018/0256134 A1 Sep. 13, 2018

(30) Foreign Application Priority Data

Mar. 9, 2017 (JP) .............................. JP2017-044724

(51) Int. Cl.
*A61B 8/00* (2006.01)
*G06T 7/00* (2017.01)
(Continued)

(52) U.S. Cl.
CPC .................. *A61B 8/54* (2013.01); *A61B 6/42* (2013.01); *A61B 6/50* (2013.01); *A61B 6/5211* (2013.01); *A61B 6/54* (2013.01); *A61B 8/08* (2013.01); *A61B 8/4245* (2013.01); *A61B 8/467* (2013.01); *A61B 8/5215* (2013.01); *A61B 8/5276* (2013.01); *A61B 8/5292* (2013.01); *G06T 7/0014* (2013.01); *G09B 23/286* (2013.01); *A61B 6/488* (2013.01); (Continued)

(58) Field of Classification Search
CPC ........... A61B 8/4254; A61B 8/00; A61B 8/42; A61B 8/54; A61B 2034/2051; A61B 34/20; A61B 8/58; Y10S 128/916; G01S 7/5205; G01S 15/899; G01S 5/10; G06T 7/001
See application file for complete search history.

(56) References Cited

U.S. PATENT DOCUMENTS 10,034,658 B2 * 7/2018 Raju .................... A61B 8/4245
2004/0068166 A1    4/2004 Faulkner et al.
(Continued)

FOREIGN PATENT DOCUMENTS

EP      1657679 A1     5/2006
JP      2001-325584 A  11/2001
(Continued)

OTHER PUBLICATIONS

Japanese Notice of Reasons for Refusal dated Jan. 21, 2020, for Japanese Patent Application No. 2017-044724, with English translation.
(Continued)

*Primary Examiner* — Joel Lamprecht
(74) *Attorney, Agent, or Firm* — Birch, Stewart, Kolasch & Birch, LLP (57) ABSTRACT

An imaging conditions acquisition unit acquires imaging conditions relevant to the positioning of an irradiation device and a radiation detector for acquiring a medical image. An imaging control unit controls the irradiation device and the like so as to acquire a pre-shot image or the medical image of the subject. A correction amount calculation unit calculates the correction amount of the imaging conditions based on the pre-shot image. A notification unit sends notification of the correction amount.

10 Claims, 8 Drawing Sheets

(51) Int. Cl.
*A61B 8/08* (2006.01)
*A61B 6/00* (2006.01)
*G09B 23/28* (2006.01)

(52) U.S. Cl.
CPC ............... *G06T 2207/10116* (2013.01); *G06T 2207/10132* (2013.01); *G06T 2207/30061* (2013.01)

(56) References Cited

U.S. PATENT DOCUMENTS

| | | | |
|---|---|---|---|
| 2005/0089137 A1* | 4/2005 | Toth | A61B 6/469 378/19 |
| 2005/0119569 A1* | 6/2005 | Ohtake | A61B 8/00 600/437 |
| 2005/0238138 A1 | 10/2005 | Imai | |
| 2006/0023929 A1 | 2/2006 | Luo et al. | |
| 2007/0253527 A1 | 11/2007 | Wink | |
| 2009/0208087 A1 | 8/2009 | Saito | |
| 2015/0057545 A1 | 2/2015 | Takagi et al. | |
| 2017/0316563 A1 | 11/2017 | Nakaya et al. | |

FOREIGN PATENT DOCUMENTS

| | | |
|---|---|---|
| JP | 2004-105739 A | 4/2004 |
| JP | 2004-135976 A | 5/2004 |
| JP | 2005-295303 A | 10/2005 |
| JP | 2006-139782 A | 6/2006 |
| JP | 2007-97665 A | 4/2007 |
| JP | 2008-508028 A | 3/2008 |
| JP | 2008-513046 A | 5/2008 |
| JP | 2010-5373 A | 1/2010 |
| JP | 2012-152417 A | 8/2012 |
| JP | 2014-117368 A | 6/2014 |
| JP | 2015-54006 A | 3/2015 |
| JP | 2015-61591 A | 4/2015 |
| WO | WO 2016/067399 A1 | 5/2016 |

OTHER PUBLICATIONS

Japanese Office Action for corresponding Japanese Application No. 2017-044724, dated Dec. 1, 2020, with English translation.
Japanese Office Action, dated Sep. 15, 2020, for corresponding Japanese Application No. 2017-044724, with an English machine translation.

* cited by examiner

AMOUNT OF PARALLEL MOVEMENT
 20 mm TO RIGHT
AMOUNT OF ROTATION
 30° CLOCKWISE

MEDICAL IMAGE CAPTURING CONTROL DEVICE, METHOD, AND PROGRAM

CROSS REFERENCE TO RELATED APPLICATIONS

The present application claims priority under 35 U.S.C. § 119 to Japanese Patent Application No. 2017-044724 filed on Mar. 9, 2017. The above application is hereby expressly incorporated by reference, in its entirety, into the present application.

BACKGROUND

Field of the Invention

The present invention relates to a medical image capturing control device, method, and program for controlling the capturing of a medical image, such as a radiographic image and an ultrasound image.

Description of the Related Art

Image diagnosis using medical images obtained by capturing a radiographic image and an ultrasound image of a patient has been performed. In addition, due to advances in medical apparatuses such as computed tomography (CT) apparatuses and magnetic resonance imaging (MRI) apparatuses, high-quality three-dimensional images with high resolution are used for image diagnosis.

On the other hand, with the recent aging of population, home healthcare is regarded important. However, in home healthcare, it is not possible to perform imaging using a CT apparatus and an MRI apparatus as described above. Therefore, the acquisition of a medical image using a radiographic image capturing apparatus, an ultrasound apparatus, and the like that are compact and portable is the key to image diagnosis in home healthcare. In home healthcare, a photographer uses a portable irradiation device, and performs imaging by arranging a radiation detector, which is for generating a radiographic image by detecting radiation transmitted through a subject, behind the subject.

In home healthcare, however, a person who captures a medical image is not a radiological technician accustomed to imaging but a doctor or a nurse unfamiliar with imaging in many cases. For this reason, it is often difficult to appropriately set the positioning of the subject.

Therefore, a method has been proposed in which a subject is imaged as a moving image using an optical camera, anatomical features of the subject (the core of the subject, the outline of the bone, and the outline of the body surface) are extracted as a guide, it is determined whether or not a past image guide matches the guide, and the photographer is notified that the past image guide matches the guide in a case where the past image guide matches the guide, so that the imaging of radiation is executed (refer to JP2014-117368A).

SUMMARY

However, in the above method disclosed in JP2014-117368A, the photographer is only notified that the guide extracted from the subject matches the guide of the past image. For this reason, since the photographer does not know how much the imaging apparatus is to be moved, it may take time to achieve appropriate positioning. On the other hand, even in the case of capturing an ultrasound image by pressing the probe of the ultrasound apparatus against the subject, it is necessary to change the positioning of the probe until an ultrasound image of an appropriate cross section can be obtained. Also in this case, since the photographer does not know how to move the probe, it may take time to achieve appropriate positioning.

The invention has been made in view of the above circumstances, and it is an object of the invention to facilitate the positioning of an imaging apparatus in capturing a medical image.

A medical image capturing control device according to the invention comprises: imaging conditions acquisition unit for acquiring imaging conditions relevant to positioning of imaging unit for acquiring a medical image of a subject by imaging the subject; imaging control unit for controlling the imaging unit so as to acquire a pre-shot image or the medical image of the subject; correction amount calculation unit for calculating a correction amount of the imaging conditions based on the pre-shot image in a case where the pre-shot image is acquired; and notification unit for sending notification of the correction amount.

The "medical image" means an image provided for diagnosis. The "pre-shot image" means an image that is acquired before the acquisition of a medical image and is used to check positioning. For example, in a case where the imaging unit acquires a radiographic image, the pre-shot image is an image acquired by irradiating the subject with radiation of a lower dose than in the case of acquiring the radiographic image. In the invention, it is assumed that the pre-shot image may mean one frame of a moving image.

In the medical image capturing control device according to the invention, the imaging control unit may control the imaging unit so as to acquire the medical image in a case where the correction amount of the imaging conditions is less than a threshold value.

In the medical image capturing control device according to the invention, the notification unit may notify that the correction amount of the imaging conditions is less than a threshold value.

In the medical image capturing control device according to the invention, the correction amount calculation unit may calculate the correction amount based on an anatomical region of the subject included in the pre-shot image.

In the medical image capturing control device according to the invention, the correction amount calculation unit may calculate the correction amount by comparing the pre-shot image with a standard image acquired under predetermined imaging conditions relevant to positioning.

In the medical image capturing control device according to the invention, the imaging unit may comprise irradiation unit for irradiating the subject with radiation and detection unit for detecting radiation transmitted through the subject to acquire a radiographic image of the subject.

In the medical image capturing control device according to the invention, the imaging unit may be ultrasound imaging unit for acquiring an ultrasound image.

The medical image capturing control device according to the invention may further comprise storage unit for storing the correction amount calculated based on the pre-shot image.

In the medical image capturing control device according to the invention, the storage unit may store the correction amount by adding the correction amount to the medical image.

In the medical image capturing control device according to the invention, the storage unit may further store information relevant to the number of times of capturing the pre-shot image.

The "information relevant to the number of times of capturing the pre-shot image" means information by which the number of times of capturing the pre-shot image can be known. Specifically, the "information relevant to the number of times of capturing the pre-shot image" may be the number of times of capturing the pre-shot image itself. In a case where the time interval at the time of acquiring the pre-shot image is known, the number of times of imaging can be calculated based on the time during which the pre-shot image has been captured. Therefore, in this case, the "information relevant to the number of times of capturing the pre-shot image" may be the time during which the pre-shot image has been captured.

In the medical image capturing control device according to the invention, the storage unit may store the correction amount by adding the number of times of capturing to supplementary information of the medical image.

A medical image capturing control method according to the invention comprises: acquiring imaging conditions relevant to positioning of imaging unit for acquiring a medical image of a subject by imaging the subject; controlling the imaging unit so as to acquire a pre-shot image or the medical image of the subject; calculating a correction amount of the imaging conditions based on the pre-shot image in a case where the pre-shot image is acquired; and sending notification of the correction amount.

In addition, a program causing a computer to execute the medical image capturing control method according to the invention may be provided.

Another medical image capturing control device according to the invention comprises: a memory for storing a command to be executed by a computer; and a processor configured to execute the stored command. The processor executes: imaging conditions acquisition processing for acquiring imaging conditions relevant to positioning of imaging unit for acquiring a medical image of a subject by imaging the subject; imaging control processing for controlling the imaging unit so as to acquire a pre-shot image or the medical image of the subject; correction amount calculation processing for calculating a correction amount of the imaging conditions based on the pre-shot image in a case where the pre-shot image is acquired; and notification processing for sending notification of the correction amount.

According to the invention, the correction amount of the imaging conditions relevant to the positioning is calculated based on the pre-shot image, and notification of the calculated correction amount is sent. Therefore, the operator can easily perform the positioning of the imaging apparatus based on the notified correction amount. In addition, by performing the positioning of the imaging apparatus based on the notified correction amount, it is possible to acquire the medical image of appropriate positioning.

DESCRIPTION OF THE PREFERRED EMBODIMENTS

Figure 1:
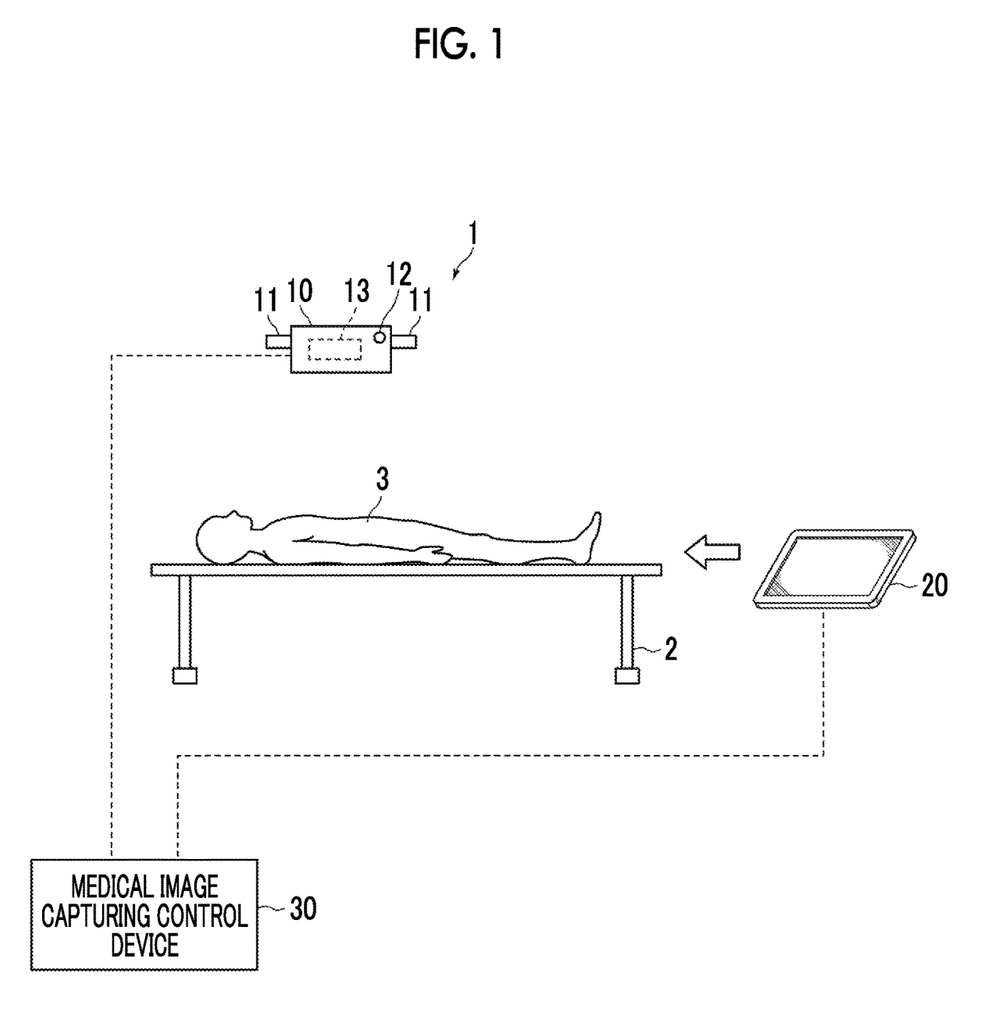
FIG. 1 is a schematic diagram of a medical image capturing system to which a medical image capturing control device according to a first embodiment of the invention is applied.

Hereinafter, embodiments of the invention will be described with reference to the accompanying diagrams. FIG. 1 is a schematic diagram of a medical image capturing system to which a medical image capturing control device according to a first embodiment of the invention is applied. As shown in FIG. 1, a medical image capturing system 1 according to the first embodiment is an apparatus for capturing a radiographic image of a subject 3, and includes an irradiation device 10, a radiation detector 20, and a medical image capturing control device 30 according to the first embodiment.

The irradiation device 10 is a portable irradiation device 10, and includes a handle 11 for making it easy for an operator to hold the irradiation device 10 and an input unit 12 for performing an operation, such as emitting radiation. Inside the housing of the irradiation device 10, not only a radiation source 13 but also a battery, a driving circuit for the radiation source 13, and the like are housed. The irradiation device 10 may be used suspended from a support device.

The radiation detector 20 can perform recording and reading of a radiographic image repeatedly. A so-called direct type radiation detector that generates an electric charge by direct reception of radiation may be used, or a so-called indirect type radiation detector that converts radiation into visible light and then converts the visible light into a charge signal may be used. As a method of reading a radiographic image signal, it is desirable to use a so-called TFT reading method in which a radiographic image signal is read by ON and OFF of a thin film transistor (TFT) switch or a so-called optical reading method in which a radiographic image signal is read by emission of reading light. However, other methods may also be used without being limited to the above methods.

In the present embodiment, in order to acquire a radiographic image of the subject 3 lying on a bed 2, the radiation detector 20 is inserted between the subject 3 and the bed 2. Then, the operator moves the irradiation device 10 while holding the irradiation device 10 by hand in order to achieve desired positioning, and gives an instruction to perform pre-imaging, in which the subject 3 is irradiated with low-dose radiation, through the input unit 12. As a result, pre-imaging is performed. At the time of pre-imaging, the subject 3 is irradiated with low-dose radiation at predetermined time intervals (for example, one at one second), and a pre-shot image P0 is acquired by the radiation detector 20. Then, in a case where the desired positioning is achieved, main imaging in which the subject 3 is irradiated with a predetermined dose of radiation is performed. As a result, a radiographic image G0 of the subject 3 is acquired.

The radiation detector 20 or the combination of the irradiation device 10 and the radiation detector 20 corresponds to imaging unit.

The medical image capturing control device 30 is realized by installing a medical image capturing control program of the invention on one computer. The computer is preferably a notebook computer so as to be able to be carried. The medical image capturing control program is distributed by being recorded on a recording medium, such as a digital versatile disc (DVD) or a compact disk read only memory (CD-ROM), and is installed onto the computer from the recording medium. Alternatively, the medical image capturing control program is stored in a storage device of a server computer connected to the network or in a network storage so as to be accessible from the outside, and is downloaded and installed onto the computer as necessary.

Figure 2:
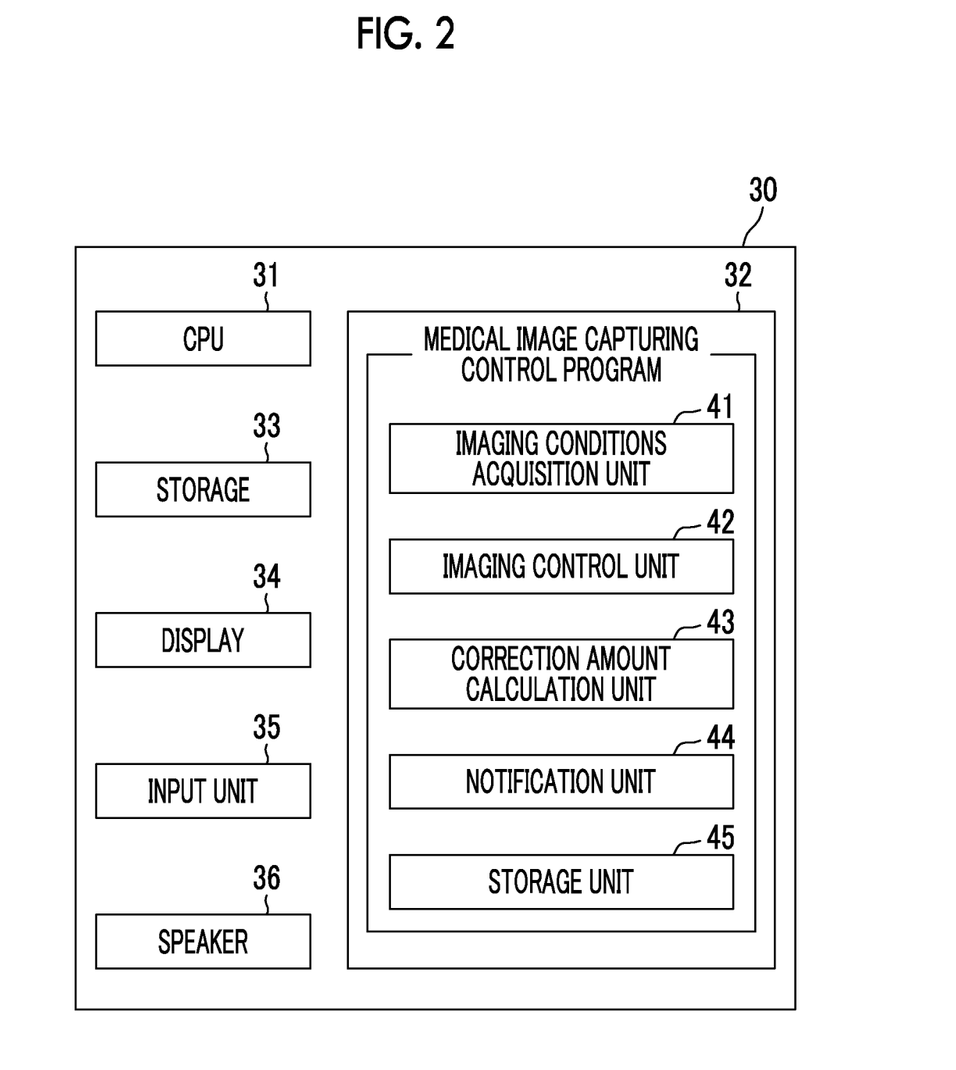
FIG. 2 is a diagram showing the schematic configuration of a medical image capturing control device realized by installing a medical image capturing control program according to the first embodiment on a computer.

FIG. 2 is a diagram showing the schematic configuration of a medical image capturing control device realized by installing a medical image capturing control program according to the first embodiment on a computer. As shown in FIG. 2, the medical image capturing control device 30 includes a central processing unit (CPU) 31, a memory 32, a storage 33, a display 34, an input unit 35, and a speaker 36 as the configuration of a standard computer.

Various kinds of information including information required for processing and radiographic images of the subject 3 acquired from the radiation detector 20 are stored in the storage 33. In the present embodiment, it is assumed that a radiographic image of the chest of the subject 3 is acquired. The storage 33 corresponds to storage unit. A medical image capturing control program is stored in the memory 32. As processing to be executed by the CPU 31, the medical image capturing control program defines imaging conditions acquisition processing for acquiring imaging conditions relevant to the positioning of the irradiation device 10 and the radiation detector 20, imaging control processing for controlling the irradiation device 10 and the radiation detector 20 so as to acquire the pre-shot image P0 or the radiographic image G0 of the subject 3, correction amount calculation processing for calculating the correction amount of the imaging conditions based on the pre-shot image P0 in a case where the pre-shot image P0 is acquired, notification processing for sending notification of the correction amount, and storage process for storing the correction amount.

The CPU 31 executes these processes according to the program, so that the computer functions as an imaging conditions acquisition unit 41, an imaging control unit 42, a correction amount calculation unit 43, a notification unit 44, and a storage unit 45. The medical image capturing control device 30 may include a plurality of processors or processing circuits that perform imaging conditions acquisition processing, imaging control processing, correction amount calculation processing, notification processing, and storage processing.

The imaging conditions acquisition unit 41 acquires imaging conditions relevant to the positioning of the irradiation device 10 and the radiation detector 20. For example, in a case where the object to be imaged is the chest of the subject 3, the radiation needs to be emitted so as to be perpendicular to the subject 3 facing the front. Therefore, the imaging conditions acquisition unit 41 acquires, as the imaging conditions relevant to the positioning, that radiation is emitted so as to be perpendicular to the subject 3. The imaging conditions acquisition unit 41 also acquires an imaging distance, which is a distance between the irradiation device 10 and the detection surface of the radiation detector 20, as one of the imaging conditions. The imaging conditions are stored in the storage 33 for each imaging procedure (imaging direction, imaging part, and the like) of a radiographic image to be imaged. The imaging conditions acquisition unit 41 acquires the imaging conditions based on the information of the imaging procedure input through the input unit 35.

Figure 3:
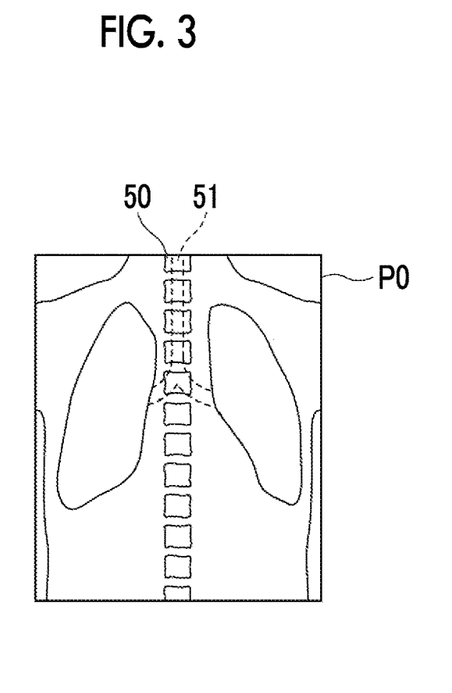
FIG. 3 is a diagram showing a radiographic image of the chest of a subject facing the front.
Figure 4:
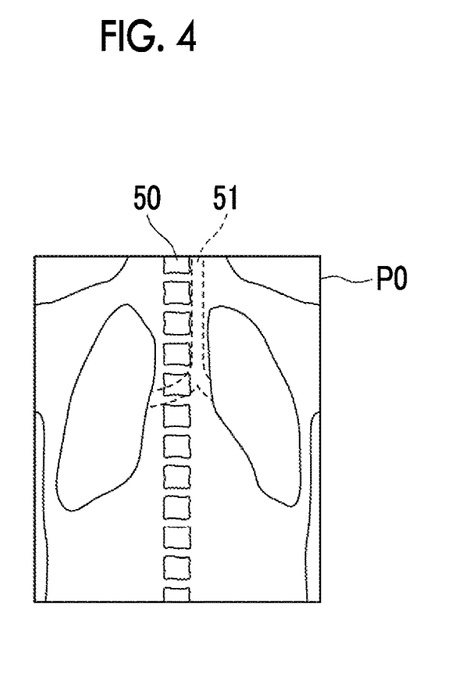
FIG. 4 is a diagram showing a radiographic image of the chest of a subject not facing the front.

In the present embodiment, the imaging conditions acquisition unit 41 acquires, as the imaging conditions, the degree of overlapping between two anatomical regions of the vertebrae and the airway included in the radiographic image of the chest. FIG. 3 is a diagram showing a radiographic image of the chest of the subject 3 facing the front, and FIG. 4 is a diagram showing a radiographic image of the chest of the subject 3 not facing the front. As shown in FIG. 3, in a case where the subject 3 faces the front, the vertebra 50 and an airway 51 completely overlap each other. However, as shown in FIG. 4, in a case where the subject 3 does not face the front, the vertebra 50 and the airway 51 do not overlap or the overlapping amount is small even if the vertebra 50 and the airway 51 overlap each other. Therefore, the imaging conditions acquisition unit 41 acquires, as the imaging conditions relevant to the positioning, that the vertebra 50 and the airway 51 completely overlap each other.

For diagnosis using the radiographic image of the chest, it is necessary for the radiographic image to include the entire lung field. Therefore, the imaging conditions acquisition unit 41 may acquire, as the imaging conditions relevant to the positioning, that the entire lung field is included.

The imaging control unit 42 controls the irradiation device 10 and the radiation detector 20 so as to acquire the pre-shot image P0 or the radiographic image G0 of the subject 3. Specifically, the imaging control unit 42 controls the driving of the irradiation device 10 and the radiation detector 20 so as to perform pre-imaging for acquiring the pre-shot image P0 by irradiating the subject 3 with radiation of a relatively low dose at predetermined time intervals. Then, as will be described later, in a case where the correction amount of the imaging conditions is less than the threshold value, main imaging is performed by irradiating the subject 3 with radiation of a predetermined dose, and the driving of the irradiation device 10 and the radiation detector 20 is controlled so as to acquire the radiographic image G0.

The correction amount calculation unit 43 calculates the correction amount of the imaging conditions based on the pre-shot image P0. Specifically, the correction amount of the imaging conditions is calculated based on the two anatomical features of the vertebra 50 and the airway 51 included in the pre-shot image P0. Here, in a case where radiation is emitted from the front of the subject 3, the vertebra 50 and the airway 51 completely overlap each other in the pre-shot image P0 as shown in FIG. 3. In this case, the pre-shot image P0 satisfies the imaging conditions relevant to positioning. On the other hand, in a case where radiation is emitted from the left side of the subject 3, the vertebra 50 and the airway 51 do not overlap or partially overlap in the pre-shot image P0 as shown in FIG. 4. In this case, the pre-shot image P0 does not satisfy the imaging conditions relevant to the positioning. Therefore, the correction amount calculation unit 43 calculates a correction amount to satisfy the imaging conditions relevant to the positioning. In the present embodiment, the amount of parallel movement of the irradiation device 10 and the amount of rotation of the radiation detector 20 are calculated as correction amounts.

Figure 5:
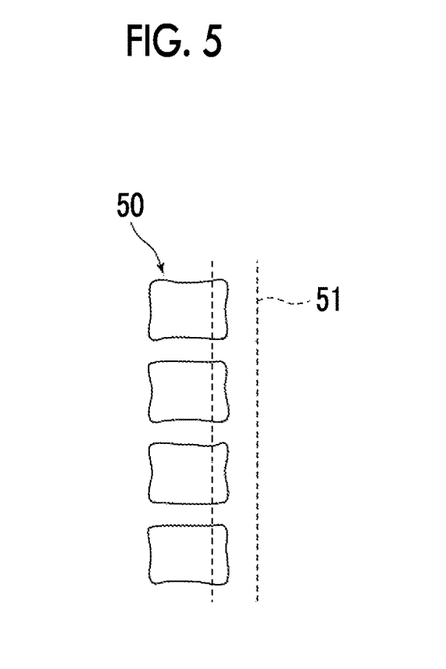
FIG. 5 is a diagram illustrating the calculation of the overlapping amount of vertebrae with respect to the airway.

In order to calculate the amount of parallel movement of the irradiation device 10, the correction amount calculation unit 43 detects the vertebra 50 and the airway 51 from the pre-shot image P0 as anatomical features, and calculates the overlapping amount of the airway 51 with respect to the vertebra 50. FIG. 5 is a diagram illustrating the calculation of the overlapping amount of vertebrae with respect to the airway. As shown in FIG. 5, the correction amount calculation unit 43 calculates the overlapping amount of the vertebrae with respect to the diameter of the airway 51. In FIG. 5, the vertebra 50 overlaps at a rate of about 30% with respect to the diameter of the airway 51. Here, conditions for capturing the radiographic image of the chest include an imaging distance. Accordingly, from the imaging distance and the overlapping ratio of the vertebra 50 to the diameter of the airway 51, the amount of movement of the irradiation device 10 necessary for the airway 51 to overlap the vertebra 50 is calculated as a correction amount. In a case where the airway 51 completely overlaps the vertebra 50, the amount of movement is the minimum 0. On the other hand, the correction amount calculation unit 43 calculates which side of the left and right sides of the vertebra 50 the airway 51 is on. In the state shown in FIG. 5, the airway 51 is on the right side of the vertebra 50. This means that the irradiation device 10 is located on the left side with respect to the subject 3. In this case, the airway 51 overlaps the vertebra 50 by moving the irradiation device 10 to the right. Therefore, in a case where the amount of movement is 20 mm, the correction amount calculation unit 43 calculates "20 mm to the right" as an amount of parallel movement. In a case where the airway 51 completely overlaps the vertebra 50, it is not necessary to adjust the positioning relevant to the parallel movement. Therefore, in a case where the airway 51 completely overlaps the vertebra 50, the amount of parallel movement is 0.

Figure 6:
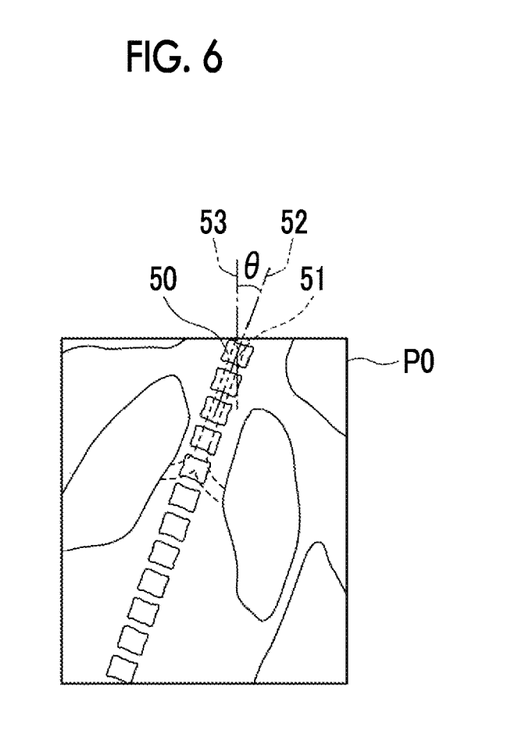
FIG. 6 is a diagram illustrating the calculation of the amount of rotation.

On the other hand, in order to calculate the amount of rotation, the correction amount calculation unit 43 calculates, as the amount of rotation, the inclination of the central axis of the airway 51 extracted from the pre-shot image P0 with respect to the vertical axis in the pre-shot image P0. FIG. 6 is a diagram illustrating the calculation of the amount of rotation. As shown in FIG. 6, the correction amount calculation unit 43 detects a central axis 52 of the airway 51, and calculates the inclination θ of the central axis 52 with respect to a vertical axis 53 of the pre-shot image P0. In the state shown in FIG. 6, the central axis 52 of the airway 51 becomes parallel to the vertical axis 53 of the pre-shot image by rotating the radiation detector 20 clockwise. Accordingly, for example, in a case where the inclination θ is 30°, the correction amount calculation unit 43 calculates "30° clockwise" as the amount of rotation. In a case where the inclination θ is 0°, it is not necessary to adjust the positioning relevant to the rotation. Therefore, in a case where the inclination θ is 0°, the correction amount calculation unit 43 sets the amount of rotation to 0.

The correction amount calculated by the correction amount calculation unit 43 is output to the imaging control unit 42 and the notification unit 44.

Figure 7:
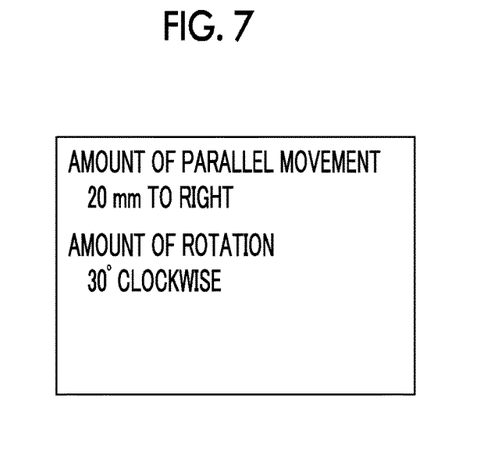
FIG. 7 is a diagram showing the amount of parallel movement and the amount of rotation that are displayed on a display.

The notification unit 44 sends notification of the correction amount calculated by the correction amount calculation unit 43. In the present embodiment, the notification unit 44 sends notification of the correction amount with sound output from the speaker 36. Specifically, the notification unit 44 sends notification of the amount of parallel movement and the amount of rotation with sound. As shown in FIG. 7, the amount of parallel movement and the amount of rotation may be displayed on the display 34 for notification. Alternatively, a display may be attached to the irradiation device 10, and notification of the correction amount may be sent to the display of the irradiation device 10.

By notification from the notification unit 44, the operator adjusts the positioning of the irradiation device 10 or the radiation detector 20 that the operator holds in his or her hand. For example, in a case where the amount of parallel movement is "20 mm to the right", the positioning relevant to the parallel movement is adjusted by moving the irradiation device 10 by 20 mm to the right with respect to the subject 3. In a case where the amount of rotation is "30° clockwise", the positioning relevant to the rotation is adjusted by rotating the radiation detector 20 by 30° clockwise. As a result of the positioning adjustment, in a case where both the amount of parallel movement and the amount of rotation become less than the threshold value and the correction amount becomes less than the threshold value, the imaging control unit 42 instructs the irradiation device 10 and the radiation detector 20 to perform main imaging. As a result, the main imaging is performed, and the radiographic image G0 of the subject 3 is acquired. In this case, the notification unit 44 may notify that the correction amount is less than the threshold value.

The storage unit 45 stores the radiographic image G0 acquired by the main imaging in the storage 33. Alternatively, the radiographic image G0 may be transmitted to an image storage server (not shown) through a network so as to be stored therein. In this case, the correction amount may be stored together with the radiographic image G0. Although the correction amount and the radiographic image G0 may be separately stored, the correction amount may be stored by adding the correction amount to the supplementary information of the radiographic image G0, such as describing the correction amount in the tag of the radiographic image G0. The amount of correction to be stored may be all the amounts of correction calculated from the start of pre-imaging until the end of the main imaging, or may be the amount of correction obtained by appropriate thinning out. In addition to the correction amount, information of the number of times of capturing the pre-shot image P0 may be stored. The information of the number of times of imaging may be the time during which pre-imaging has been performed as well as the number of times of imaging. In the present embodiment, since the time interval of pre-imaging is known, the number of times of imaging can be calculated in a case where the time during which pre-imaging has been performed is known.

Figure 8:
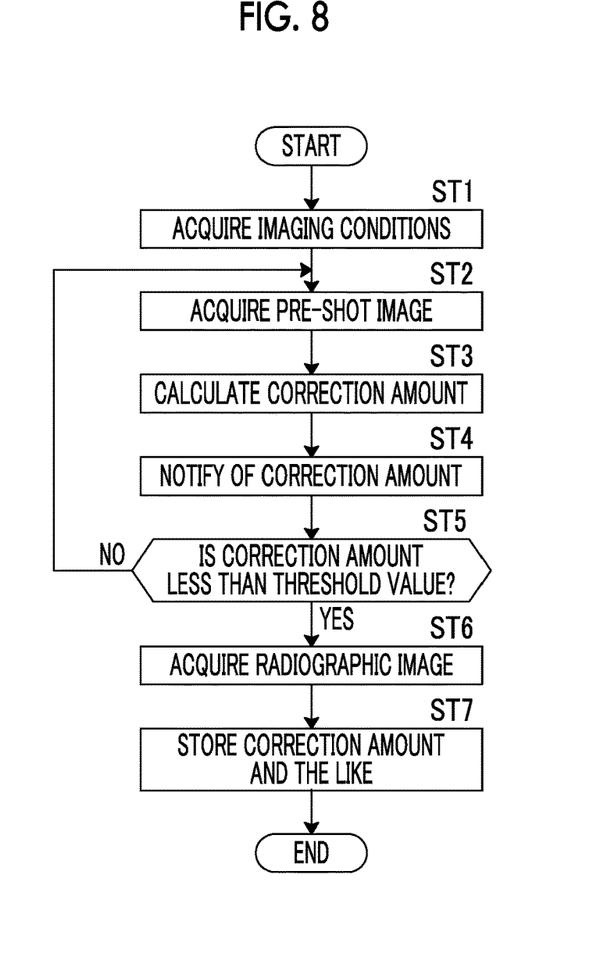
FIG. 8 is a flowchart showing the process performed in the first embodiment.

Next, the process performed in the first embodiment will be described. FIG. 8 is a flowchart showing the process performed in the first embodiment. In a case where an imaging instruction is given to the medical image capturing control device 30, the imaging conditions acquisition unit 41 acquires the imaging conditions relevant to the positioning of the irradiation device 10 and the radiation detector 20 (step ST1). Then, the operator inserts the radiation detector 20 between the subject 3 and the bed 2, and holds the irradiation device 10 by hand and gives an instruction of pre-imaging. Then, the imaging control unit 42 acquires the pre-shot image P0 (step ST2). Then, the correction amount calculation unit 43 calculates the correction amount of the imaging conditions based on the pre-shot image P0 (step ST3). Then, the notification unit 44 sends notification of the correction amount calculated by the correction amount calculation unit 43 (step ST4).

On the other hand, the correction amount is also input to the imaging control unit 42, and the imaging control unit 42 determines whether or not the correction amount is less than the threshold value (step ST5). In a case where step ST5 is negative, the process returns to step ST2. In a case where step ST5 is positive, the imaging control unit 42 performs main imaging to acquire the radiographic image G0 (step ST6). Then, the storage unit 45 stores the radiographic image G0, the correction amount, and the number of times of capturing the pre-shot image (stores the correction amount and the like, step ST7), and the process is ended.

As described above, in the present embodiment, the correction amount of the imaging conditions relevant to the positioning is calculated based on the pre-shot image P0, and notification of the calculated correction amount is sent. Therefore, the operator can easily perform the positioning of the irradiation device 10 and the radiation detector 20 based on the notified correction amount. In addition, by performing the positioning of the irradiation device 10 and the radiation detector 20 based on the notified correction amount, it is possible to acquire the radiographic image G0 of appropriate positioning.

By performing main imaging to acquire the radiographic image G0 in a case where the correction amount of the imaging conditions is less than the threshold value, the operator can acquire the required radiographic image G0 without being conscious of the imaging operation.

By storing the correction amount calculated based on the pre-shot image P0, it is possible to check how much the operator has corrected the positioning to acquire the radiographic image G0. Therefore, it is possible to easily check the strong and weak points of positioning by the operator.

By storing the number of times of capturing the pre-shot image P0, it is possible to manage the exposure dose of radiation to the subject 3.

Figure 9:
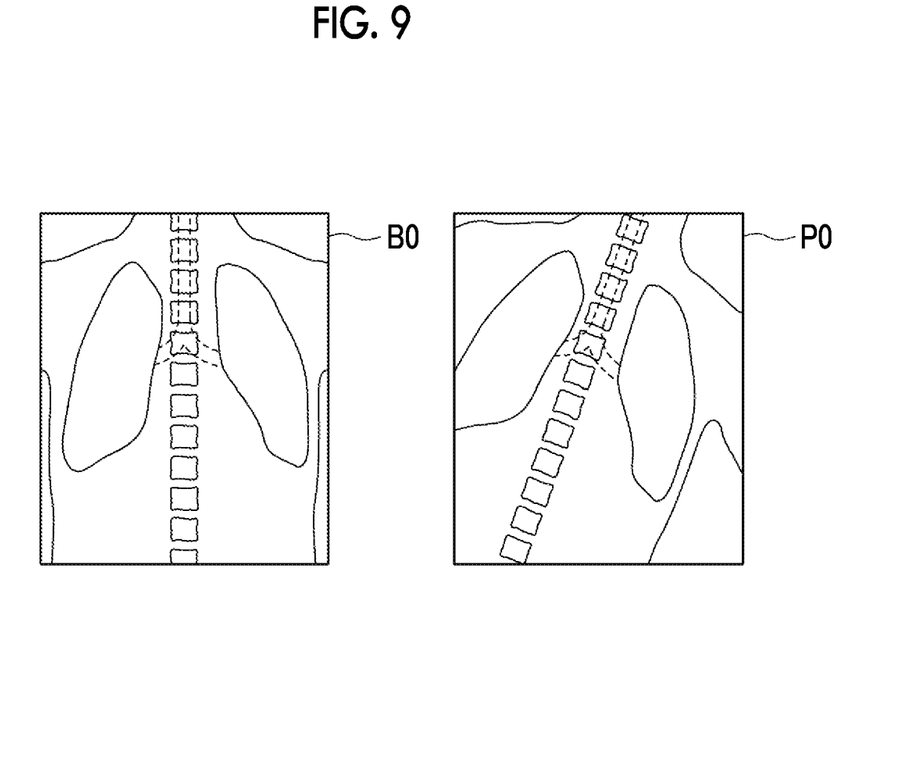
FIG. 9 is a diagram showing a standard image and a pre-shot image.

In the embodiment described above, the correction amount is calculated based on the positional relationship between the two anatomical features, that is, the vertebrae and the airway that are included in the pre-shot image P0. However, the correction amount may be calculated by comparing the pre-shot image P0 with the standard image. For example, a standard image B0 shown in FIG. 9 is stored in the storage 33. The standard image B0 is acquired under the imaging conditions that are predetermined positioning. The imaging conditions acquisition unit 41 acquires the standard image B0 as the imaging conditions. The correction amount calculation unit 43 deforms the pre-shot image P0 so as to match the standard image B0, and calculates deformation parameters relevant to the parallel movement, rotation, and enlargement and reduction of the pre-shot image P0 as correction amounts. The parameter of parallel movement is the amount of movement in each of two axis directions for moving the irradiation device 10 in parallel to the detection surface of the radiation detector 20. The parameter of rotation is a rotation angle of the irradiation device 10 with respect to the axis perpendicular to the detection surface of the radiation detector 20. The parameter of enlargement and reduction is the amount of movement of the irradiation device 10 with respect to the radiation detector 20. In the embodiment described above, the correction amount is calculated based on the vertebrae and the airway. However, the correction amount may also be calculated based on, for example, the thorax and the diaphragm. Alternatively, the correction amount may be calculated based on the left hilar and right hilar in the lung. In this case, the imaging conditions relevant to positioning are acquired based on the thorax and the diaphragm for the former case, and are acquired based on the left hilar and right hilar for the latter case.

In the embodiment described above, the correction amount is calculated based on the two anatomical regions of the vertebrae and the airway. However, the correction amount may also be calculated based on one anatomical region or three or more anatomical regions.

Figure 10:
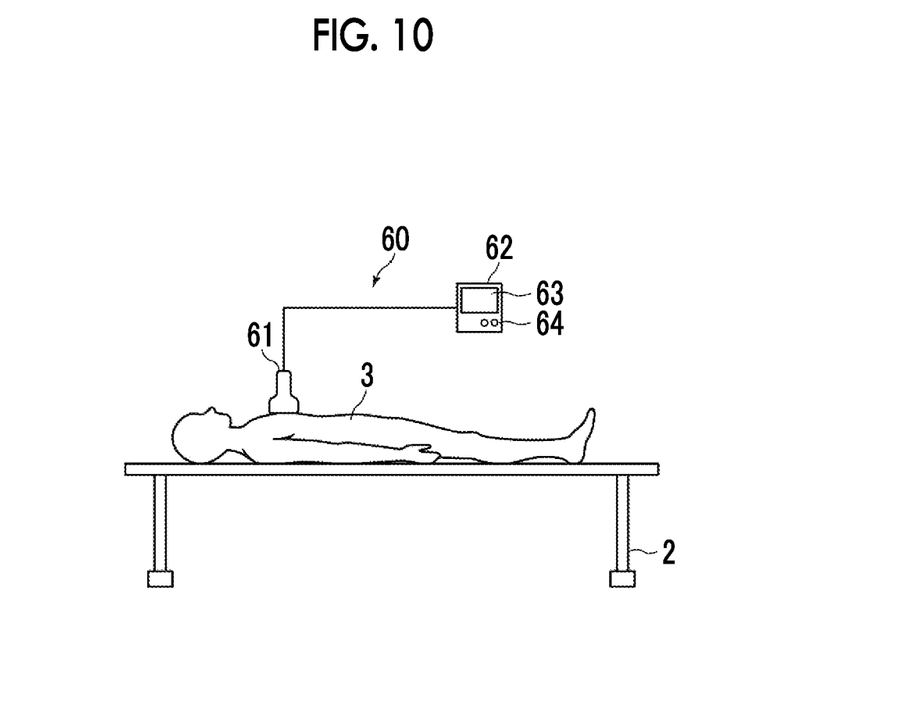
FIG. 10 is a schematic diagram of a medical image capturing system to which a medical image capturing control device according to a second embodiment of the invention is applied.

In addition, although the radiographic image is used as a medical image in the embodiment described above, an ultrasound image may be used. Hereinafter, this will be described as a second embodiment. FIG. 10 is a schematic diagram of a medical image capturing system to which a medical image capturing control device according to a second embodiment of the invention is applied. As shown in FIG. 10, a medical image capturing system 1 according to the second embodiment is an apparatus for capturing an ultrasound image of the subject 3, and includes an ultrasound imaging apparatus 60. In the second embodiment, explanation will be given on the assumption that an ultrasound image of the heart of the subject 3 is acquired.

The ultrasound imaging apparatus 60 includes an ultrasound probe (probe) 61 and an operating device 62 connected to the probe 61. The operating device 62 corresponds to the medical image capturing control device according to the second embodiment.

The probe 61 transmits an ultrasound wave toward the subject 3, receives an ultrasound wave reflected from the inside of the subject 3, and outputs a detection signal to the operating device 62.

The operating device 62 generates an ultrasound image based on the detection signal acquired by the probe 61. The operating device 62 includes a display 63 for displaying an ultrasound image and an input unit 64 for performing various inputs. The operating device 62 is realized by installing a medical image capturing control program of the invention on a computer mounted thereinside.

Figure 11:
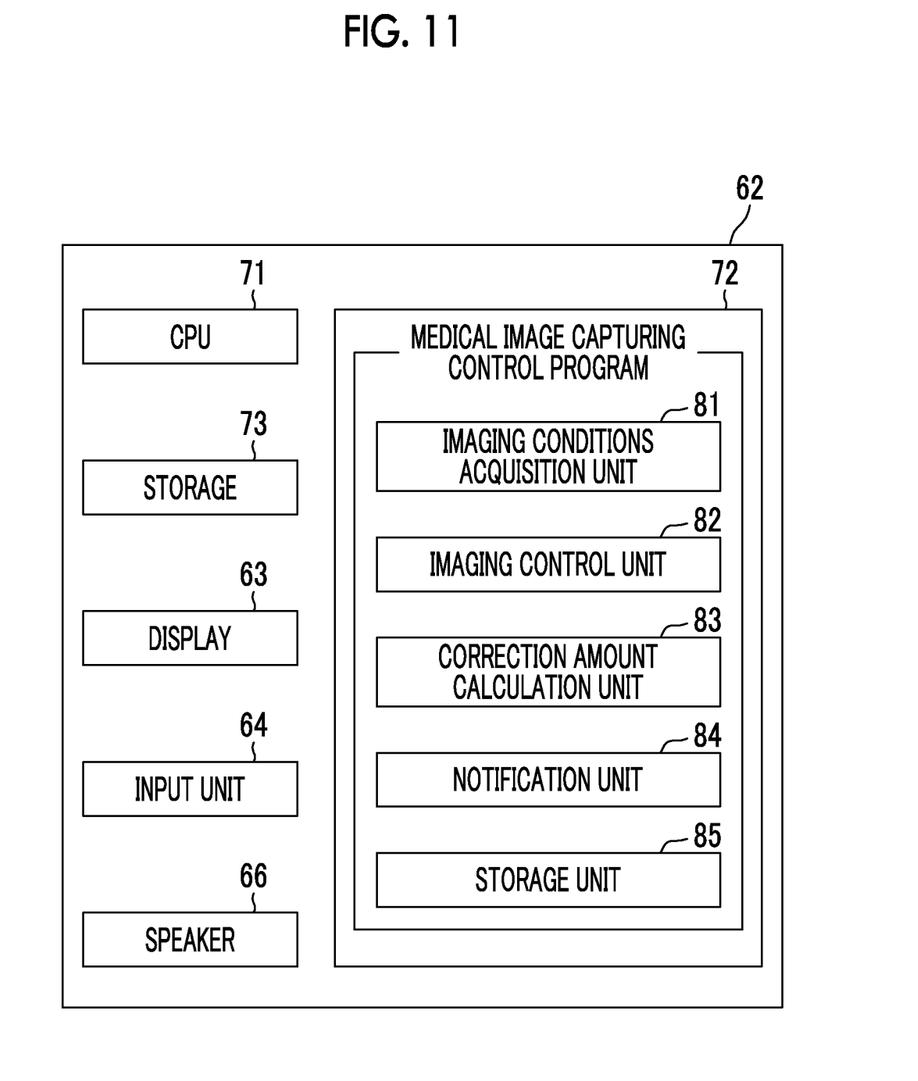
FIG. 11 is a diagram showing the schematic configuration of an operating device realized by installing a medical image capturing control program according to the second embodiment on a computer.

FIG. 11 is a diagram showing the schematic configuration of a medical image capturing control device realized by installing a medical image capturing control program according to the second embodiment on a computer. As shown in FIG. 11, the operating device 62 includes a CPU 71, a memory 72, and a storage 73. Since the CPU 71, the memory 72, and the storage 73 have the same configuration as the CPU 31, the memory 32, and the storage 33 shown in FIG. 2, the detailed explanation thereof will be omitted. The medical image capturing control program according to the second embodiment is stored in the memory 72. The CPU 71 executes the processing of the medical image capturing control program so that the operating device 62 functions as an imaging conditions acquisition unit 81, an imaging control unit 82, a correction amount calculation unit 83, a notification unit 84, and a storage unit 85. The imaging conditions acquisition unit 81, the imaging control unit 82, the correction amount calculation unit 83, the notification unit 84, and the storage unit 85 correspond to the imaging conditions acquisition unit 41, the imaging control unit 42, the correction amount calculation unit 43, the notification unit 44, and the storage unit 45 shown in FIG. 2, respectively. The operating device 62 also includes a speaker 66.

Figure 12:
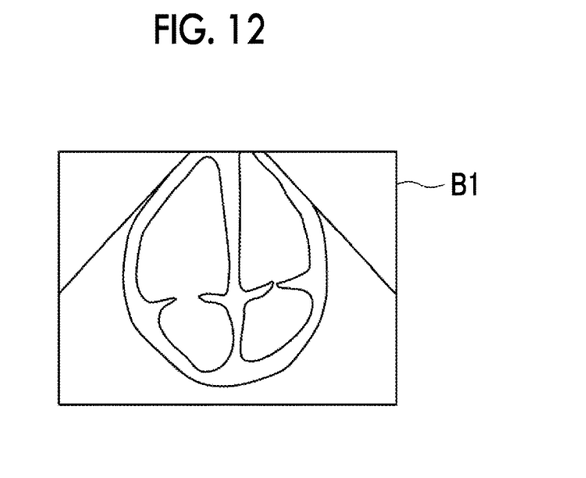
FIG. 12 is a diagram showing a standard image of an ultrasound image of the heart.

In the second embodiment, the imaging conditions acquisition unit 81 acquires the imaging conditions relevant to the positioning of the probe 61. In the second embodiment, imaging conditions are assumed in which four rooms of the heart, that is, the left atrium, the left ventricle, the right atrium, and the right ventricle, are included in an ultrasound image. Also in the second embodiment, the imaging conditions are stored in the storage 73 for each part to be imaged. The imaging conditions acquisition unit 81 acquires the imaging conditions based on the information of a part input through the input unit 64. In the second embodiment, as shown in FIG. 12, a standard image B1 including four rooms of the heart is acquired as the imaging conditions.

The imaging control unit 82 acquires a pre-shot image and an ultrasound image of the subject 3. Specifically, the imaging control unit 82 generates a pre-shot image by imaging the signal detected by the probe 61 at a predetermined frame rate (for example, 30 fps). Then, as will be described later, in a case where the correction amount of the imaging conditions is less than the threshold value, an image generated at that timing is acquired as an ultrasound image. In the second embodiment, both the pre-shot image and the ultrasound image are the same image. Therefore, in the second embodiment, U0 is given to a stored ultrasound image as a reference symbol, and an ultrasound image to be a pre-shot image is referred to as a pre-shot image and P1 is given to the ultrasound image as a reference symbol.

The correction amount calculation unit 83 calculates the correction amount of the imaging conditions based on a pre-shot image P1. In the second embodiment, a plurality of reference images associated with the correction amount for matching with the standard image B1 are stored in the storage 33. The correction amount calculation unit 83 calculates a correlation value between the pre-shot image and the reference image. As the correlation value, it is possible to use an absolute value of a difference between corresponding pixels, a value obtained by squaring a difference between pixels, and the like. Then, the correction amount calculation unit 83 calculates the correction amount associated with the reference image, which has the largest correlation (smallest correlation value) with the pre-shot image P1, as a required correction amount. As the correction amount in the second embodiment, at least one of the amount of parallel movement of the probe 61, the amount of rotation of the probe 61, pressure for pressing the probe 61 against the subject 3, or the like can be used. The correction amount calculated by the correction amount calculation unit 83 is output to the imaging control unit 82.

In the second embodiment, the pre-shot image P1 is acquired at a predetermined frame rate. Therefore, the correction amount calculation unit 83 calculates the correction amount while thinning out the pre-shot image P1 at predetermined frame intervals. For example, the correction amount is calculated once in every 10 frames of the pre-shot image P1. In this manner, it is possible to reduce the amount of calculation in calculating the correction amount. In addition, the correction amount may be calculated for all of the acquired pre-shot images P1.

The notification unit 84 sends notification of the correction amount calculated by the correction amount calculation unit 83, similarly to the notification unit 44 in the first embodiment described above.

The storage unit 85 stores the ultrasound image U0 in the storage 73, similarly to the storage unit 45 in the first embodiment described above.

Figure 13:
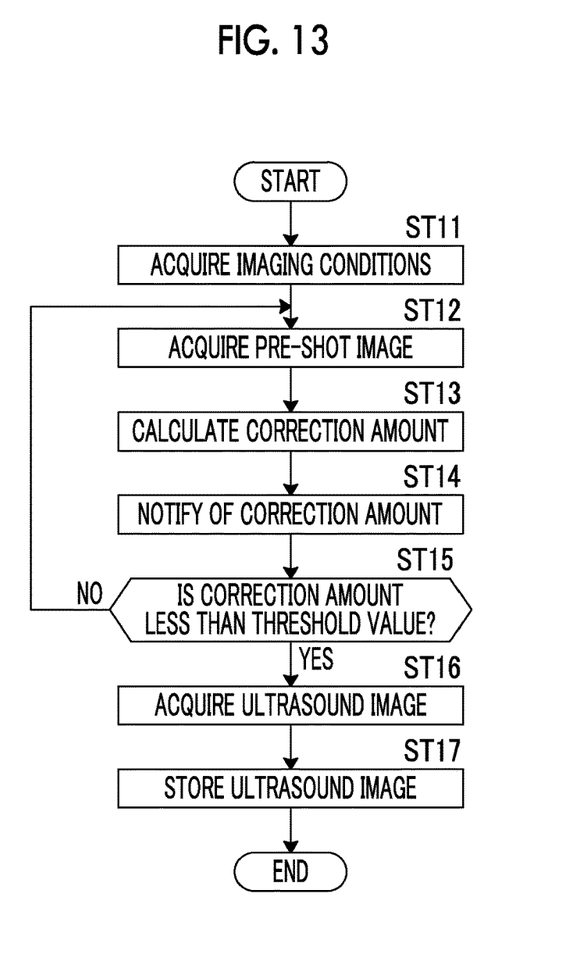
FIG. 13 is a flowchart showing the process performed in the second embodiment.

Next, the process performed in the second embodiment will be described. FIG. 13 is a flowchart showing the process performed in the second embodiment. In a case where an imaging instruction is given by the operating device 62, the imaging conditions acquisition unit 81 acquires the imaging conditions relevant to the positioning of the probe 61 (step ST11). Then, the operator moves the probe 61 while pressing the probe 61 against the subject 3. As a result, the imaging control unit 82 acquires the pre-shot image P1 showing the ultrasound image of the moved position (step ST12). The pre-shot image P1 acquired in step ST12 is for calculating the correction amount. Then, the correction amount calculation unit 83 calculates the correction amount of the imaging conditions based on the pre-shot image P1 (step ST13). Then, the notification unit 84 sends notification of the correction amount calculated by the correction amount calculation unit 83 (step ST14).

On the other hand, the correction amount is also input to the imaging control unit 82, and the imaging control unit 82 determines whether or not the correction amount is less than the threshold value (step ST15). In the second embodiment, the correction amount includes the amount of parallel movement of the probe 61, the amount of rotational movement of the probe 61, the pressure of the probe 61, and the like. The determination in step ST15 may be made by determining whether or not all of the amount of parallel movement, the amount of rotational movement, the pressure, and the like included in the correction amount are less than the threshold value. Alternatively, the determination in step ST15 may be made by determining whether or not at least one of the amount of parallel movement, the amount of rotational movement, the pressure, or the like are less than the threshold value.

In a case where step ST15 is negative, the process returns to step ST12. The processing of steps ST12 to ST15 is performed at intervals of several frames as described above. In a case where step ST15 is positive, the imaging control unit 82 acquires the pre-shot image P1, which is currently being captured, as the ultrasound image U0 (step ST16). Then, the storage unit 85 stores the ultrasound image U0 (step ST17), and the process is ended.

In the first and second embodiments described above, the radiographic image G0 or the ultrasound image U0 is acquired in a case where the correction amount is less than the threshold value. However, the operator may determine the timing of imaging based on the notified correction amount and give an instruction of imaging or an instruction of image storage to acquire and store the radiographic image G0 or the ultrasound image U0. In this case, it is preferable that the notification units 44 and 84 notify that the correction amount is less than the threshold value. As a result, the operator can give an instruction of imaging or an instruction of image storage more easily.

Hereinafter, the effect of the present embodiment will be described.

By acquiring the medical image in a case where the correction amount of the imaging conditions is less than the threshold value, the operator can acquire the required medical image without being conscious of imaging.

By storing the correction amount calculated based on the pre-shot image, it is possible to check how much the operator has corrected the positioning to acquire the medical image. Therefore, it is possible to easily check the strong and weak points of positioning by the operator.

By storing the number of times of capturing the pre-shot image, it is possible to manage the exposure dose of radiation to the subject particularly in a case where the medical image is a radiographic image.

What is claimed is:

1. A medical image capturing control device, comprising:
    processing circuitry configured to:
        acquire imaging conditions relevant to positioning of imaging unit for acquiring a medical image of a subject by imaging the subject, the imaging unit comprising an irradiation device for irradiating the subject with radiation and a radiation detector for detecting radiation transmitted through the subject to acquire a radiographic image of the subject;

control the imaging unit so as to acquire a pre-shot image or the medical image of the subject;

calculate a correction amount of the imaging conditions based on the pre-shot image in a case where the pre-shot image is acquired; and send notification of the correction amount, and storage for storing the correction amount calculated based on the pre-shot image and information relevant to the number of times of capturing the pre-shot image.

2. The medical image capturing control device according to claim 1, wherein the processing circuitry controls the imaging unit so as to acquire the medical image in a case where the correction amount of the imaging conditions is less than a threshold value.

3. The medical image capturing control device according to claim 1, wherein the processing circuitry notifies that the correction amount of the imaging conditions is less than a threshold value.

4. The medical image capturing control device according to claim 1, wherein the processing circuitry calculates the correction amount based on an anatomical region of the subject included in the pre-shot image.

5. The medical image capturing control device according to claim 1, wherein the processing circuitry calculates the correction amount by comparing the pre-shot image with a standard image acquired under predetermined imaging conditions relevant to positioning.

6. The medical image capturing control device according to claim 1, wherein the storage stores the correction amount by adding the correction amount to supplementary information of the medical image.

7. The medical image capturing control device according to claim 1, wherein the storage stores the correction amount by adding the number of times of capturing to supplementary information of the medical image.

8. The medical image capturing control device according to claim 1, wherein the processor is configured to:

determine first imaging conditions when the pre-shot image was obtained based on the pre-shot image;

obtain second imaging conditions that must be satisfied when obtaining the medical image from the storage; and calculate the correction amount based on the first imaging conditions and the second imaging conditions.

9. A medical image capturing control method, comprising:

acquiring imaging conditions relevant to positioning of imaging unit for acquiring a medical image of a subject by imaging the subject, the imaging unit comprising an irradiation device for irradiating the subject with radiation and a radiation detector for detecting radiation transmitted through the subject to acquire a radiographic image of the subject;

controlling the imaging unit so as to acquire a pre-shot image or the medical image of the subject;

calculating a correction amount of the imaging conditions based on the pre-shot image in a case where the pre-shot image is acquired;

sending notification of the correction amount; and storing the correction amount calculated based on the pre-shot image and information relevant to the number of times of capturing the pre-shot image.

10. A non-transitory computer-readable recording medium having stored therein a medical image capturing control program causing a computer to execute:

a step of acquiring imaging conditions relevant to positioning of imaging unit for acquiring a medical image of a subject by imaging the subject, the imaging unit comprising an irradiation device for irradiating the subject with radiation and a radiation detector for detecting radiation transmitted through the subject to acquire a radiographic image of the subject;

a step of controlling the imaging unit so as to acquire a pre-shot image or the medical image of the subject;

a step of calculating a correction amount of the imaging conditions based on the pre-shot image in a case where the pre-shot image is acquired;

a step of sending notification of the correction amount; and a step of storing the correction amount calculated based on the pre-shot image and information relevant to the number of times of capturing the pre-shot image.

* * * * *